United States Patent [19]
Gruber et al.

[11] Patent Number: 5,962,743
[45] Date of Patent: Oct. 5, 1999

[54] PROCESS FOR PREPARING ACYLAROMATIC COMPOUNDS

[75] Inventors: John Myron Gruber, Mountain View; Robert Seemayer, Belmont, both of Calif.

[73] Assignee: Catalytica Pharmaceuticals, Inc., Mountain View, Calif.

[21] Appl. No.: 09/191,412

[22] Filed: Nov. 12, 1998

[51] Int. Cl.⁶ .......................... C07C 221/00; C07C 45/00
[52] U.S. Cl. ........................... 568/319; 564/344; 564/343
[58] Field of Search .............................. 568/319; 564/344, 564/343

[56] References Cited

U.S. PATENT DOCUMENTS

| | | |
|---|---|---|
| 2,475,564 | 7/1949 | Hartough et al. . |
| 4,599,452 | 7/1986 | Colquhoun et al. . |
| 5,041,616 | 8/1991 | Sumner . |
| 5,235,068 | 8/1993 | Minwi et al. . |
| 5,347,047 | 9/1994 | Siegel et al. . |
| 5,434,310 | 7/1995 | Waldmann et al. . |
| 5,621,146 | 4/1997 | Fukumoto . |

FOREIGN PATENT DOCUMENTS

| | | |
|---|---|---|
| 0252436 | 12/1985 | Japan . |
| 1282335 | 12/1986 | Japan . |
| 473023 | 3/1992 | United Kingdom . |

*Primary Examiner*—Paul J. Killos
*Attorney, Agent, or Firm*—John Grate; Al Jecminek

[57] ABSTRACT

This invention provides a process for preparing acylaromatics comprising reacting an aromatic compound with a carboxylic acid in the presence of a reaction medium comprising polyphosphoric acid and a strong protic acid. In one embodiment, the invention provides a process for preparing a para-acyl phenoxyethylamine comprising the steps of reacting a 2-phenoxyethyl compound bearing a leaving group on the ethyl 1-position with a carboxylic acid in the presence of a reaction medium comprising polyphosphoric acid and a strong protic acid, to form apara-acyl phenoxyethyl intermediate bearing the leaving group; and reacting the para-acyl phenoxyethyl intermediate with an amine that substitutes for the leaving group to form the para-acyl phenoxyethylamine.

33 Claims, No Drawings

PROCESS FOR PREPARING ACYLAROMATIC COMPOUNDS

FIELD OF THE INVENTION

This invention relates generally to the chemical preparation of acylaromatic compounds by aromatic acylation. More specifically, it relates to aromatic acylations wherein the acyl group is provided by a carboxylic acid reactant. Acylaromatic compounds are valuable intermediates and products in many sectors of the chemical industry. In particular, para-acyl phenoxyethyl-amine compounds are valuable as intermediates in the preparation of various active pharmaceutical ingredients. 1-[4-[2-(N,N-dimethylamino) ethoxy]-phenyl]-2-phenyl-1-butanone is a precursor to the estrogen receptor modulators tamoxifen and droloxifene.

BACKGROUND OF THE INVENTION

Throughout this application, various publications, patents, and published patent applications are referred to by an identifying citation; full citations for these documents may be found at the end of the specification immediately preceding the claims. The disclosures of the publications, patents, and published patent specifications referenced in this application are hereby incorporated by reference into the present disclosure to more fully describe the state of the art to which this invention pertains.

The most important method used for the commercial preparation of acylaromatic compounds is Friedel-Crafts aromatic acylation. In the typical Friedel-Crafts aromatic acylation, a Lewis acid reagent, such as aluminum trichloride ($AlCl_3$) is added to a mixture of an acyl chloride and an aromatic compound to cause a vigorous reaction that, after hydrolytic quenching, generates the acylaromatic.

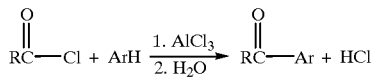

The reaction is usually conducted in an inert solvent such as chlorinated solvents, like dichloromethane, and deactivated aromatics, typically nitrobenzene. A little more than a molar equivalent of the Lewis acid reagent is required, since the ketone product forms a strong Lewis acid-base complex with the reagent. The addition of water and acid to the reaction mixture after the reaction destroys this complex and liberates the ketone. Such Friedel-Crafts aromatic acylation reactions are often highly efficient and selective reactions and are commonly used despite their substantial undesirable features.

Aluminum chloride, the most effective and commonly used Lewis Acid reagent for this reaction, is an unpleasant, hazardous material to handle. Large quantities of aluminum chloride, at least stoichiometric, are usually needed for the acylation. In some acylation reactions two or three times the stoichiometric amount of aluminum chloride has to be used.

Aluminum chloride is in general not recovered for reuse. At completion, the reaction is quenched with a considerable volume of water. This requires the use of a much larger reactor, to accommodate the quench volume, or the use of a second reactor 1.5–2 times larger than the first. There is a considerable negative impact associated with the tying up of equipment and lengthening of the reaction cycles resulting from this quench step. Also considerable cooling is required during the quench process. Disposal of the considerable aqueous aluminum waste products can be a problem for companies involved in the Friedel-Crafts on only an occasional basis.

The conventional Friedel-Crafts aromatic acylation typically utilizes an acyl halide reactant, usually an acyl chloride. This must be first prepared from the carboxylic acid, typically using a reagent like thionyl chloride that is not a particularly desirable compound to handle on large scale. Hydrogen chloride gas, is released in the formation of formation of the acyl chloride (along with $SO_2$ when using thionyl chloride) and in the acylation reaction, and must be abated with an acid gas scrubber.

Also, the solvent of choice for many such conventional Friedel-Crafts acylation processes is a chlorinated hydrocarbon, such as dichloromethane, whose use in industrial synthesis has become increasingly less acceptable.

Intramolecular Friedel-Crafts acylation may also be used to effect ring closure of arylalkanoic acids and their acyl halide derivatives. When the acyl reactant is an acyl halide, the reagent is typically a Lewis acid such as $AlCl_3$ or $ZnBr_2$. When the acyl reactant is a carboxylic acid, the reagent is typically a protic acid, such as hydrogen fluoride, methanesulfonic acid, or polyphosphoric acid (Yamoto et al., 1991). A 1:10 by weight solution of phosphorus pentoxide in methanesulfonic acid has been examined as an alternative to polyphosphoric acid in similar acylation reactions (Eaton et al., 1973).

Many heterocyclic aromatic systems, including firans, thiophenes, pyrans, and pyrroles can be acylated in. good yield by Friedel-Crafts acylation.

Reagents other than acid chlorides, such as carboxylic acids, anhydrides, and ketenes have also been used successfully. With active substrates, such as aryl ethers, the reaction can sometimes be carried out with catalytic amounts of the reagent. Typically, the catalyst is a Lewis acid, such as $AlCl_3$, $BF_3$, $FeCl_3$ and $ZnCl_2$, but other catalysts, including protic acids have been used.

The estrogen modulator drugs known as tamoxifen (1,2-diphenyl-1-[4-[2-(N,N,-dimethylamino) ethoxy]phenyl]-1-butene) and droloxifene (3-[-1-[4-[2-(N,N,-dimethylamino) ethoxy]phenyl]-2-phenyl-1-butenyl]phenol) are typically prepared via a versatile acylaromatic intermediate 1-[4-[2-(N,N-dimethyl-amino) ethoxy]phenyl]-2-phenyl-1-butanone (see Tiovola et al., 1996).

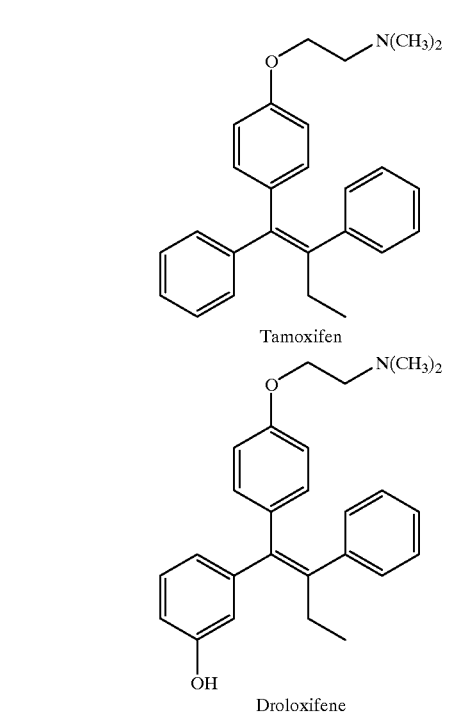

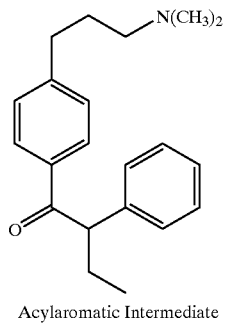

Acylaromatic Intermediate

This acylaromatic intermediate is typically prepared by a conventional Friedel-Crafts acylation reaction. The conventional synthetic pathway is shown below. Greater than two mole equivalents of $AlCl_3$ are required as the amine function complexes with one equivalent and the ketone group of the product complexes with a second equivalent.

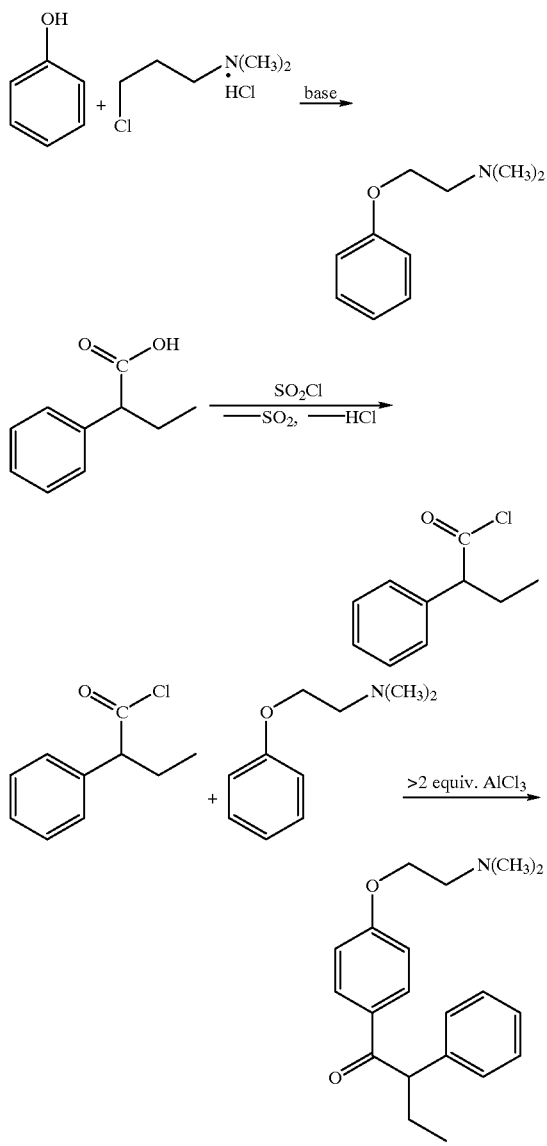

Recently, alternative synthetic routes to this acylaromatic have been investigated to avoid the disadvantages of the conventional Friedel-Crafts acylation reaction. Some have adapted the use of anhydrides, specifically trifluoroacetic acid anhydride, in acylation reactions (see Gaili, 1979).

In one method (Smyth et al., 1997), N,N-dimethyl-2-phenoxyethylamine and 2-phenylbutyric acid are the starting materials, and the reaction involves in situ formation of the trifluoroacetyl mixed anhydride, as shown below.

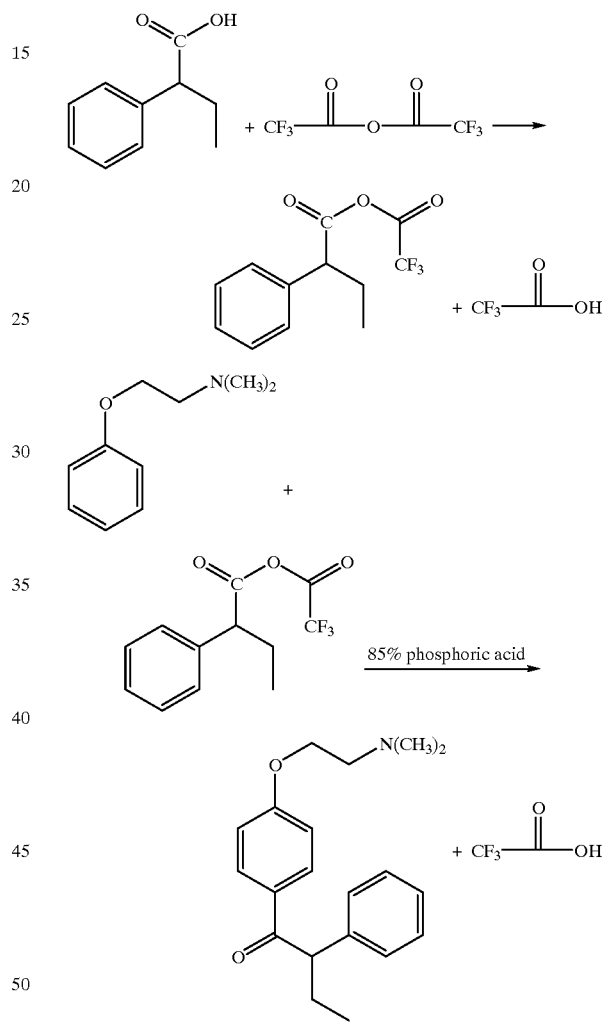

Here, excess trifluoroacetic acid anhydride (TFAA) is added to one equivalent of 2-phenylbutyric acid to form the mixed anhydride and trifluoroacetic acid (TFA). One equivalent of N,N-dimethyl-2-phenoxyethylamine is then added, followed by one equivalent of 85% phosphoric acid. The mixture is then refluxed to yield the desired ketone.

In another method (McCague, 1985), the trifluoroacetyl mixed anhydride is reacted, instead, with 2-phenoxyethyl chloride, and the product is next reacted with dimethylamine to yield the desired ketone, as shown below:

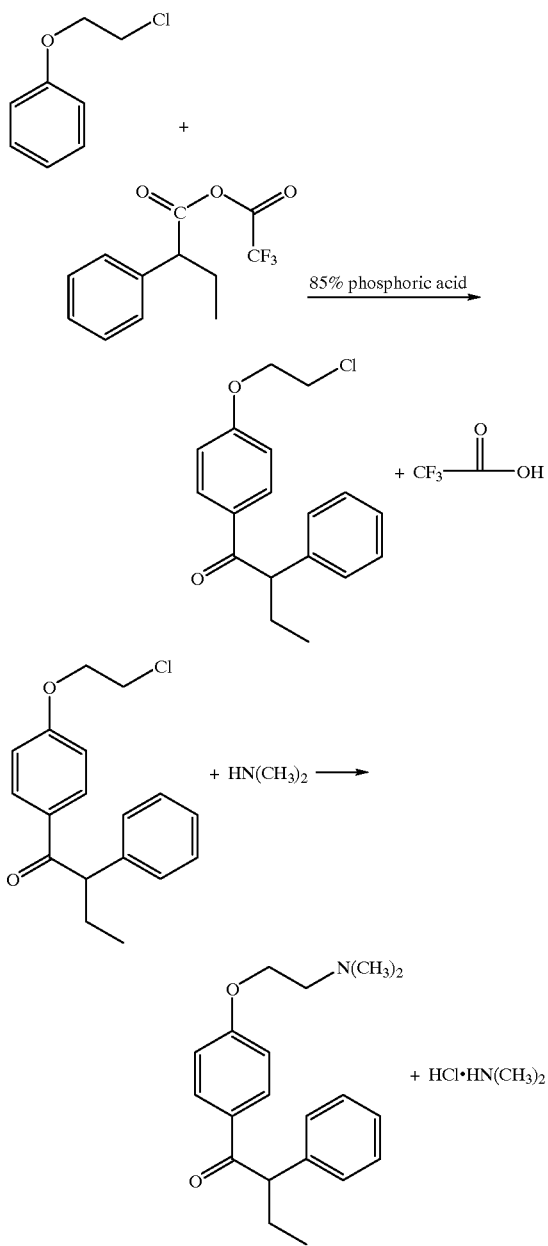

These processes using trifluoroacetic anhydride are not economically attractive relative to conventional Friedel-Crafts acylation due to the expense of trifluoroacetic anhydride. Recognizing this, Smyth et al. proposed to recycle the trifluoroacetic acid produced in the process by distillation from the acylation reaction mixture, reaction with 4+equivalents of phosphorus pentoxide to reform trifluoroacetic anhydride, and recovery of the trifluoroacetic anhydride by distillation. While this may improve the economics of the processes based on trifluoroacetic anhydride, it is none the less still a costly and undesirable operation.

OBJECTS OF THE INVENTION

The object of this invention is to provide an economically preferable, effective and efficient process for the preparation acylaromatics. A further object of this invention is to provide a process for the preparation of acylaromatics that avoids the use of aluminum chloride and other Lewis Acid reagents conventionally used for Friedel-Crafts aromatic acylation. Another object of this invention is to provide an efficient process for the preparation of acylaromatics wherein the acyl group is provided by a carboxylic acid reactant, rather than requiring an acyl halide. Other objects and advantages will become apparent to persons skilled in the art and familiar with the background references from a careful reading of this specification.

SUMMARY OF THE INVENTION

In its most general terms, the present invention provides a process for preparing acylaromatics of the formula $R^1C(=O)Ar^1$ comprising reacting an aromatic compound of the formula $HAr^1$, wherein $Ar^1$ is an aryl group, with a carboxylic acid of the formula $R^1C(=O)OH$, wherein $R^1$ is a hydrocarbyl group, in the presence of a reaction medium comprising polyphosphoric acid and a strong protic acid, to form the acylaromatic compound. The inventors surprisingly discovered that while neither polyphosphoric acid nor a strong protic acid alone as the reaction medium provided the desired aromatic acylation reaction, the mixture of polyphosphoric acid and the strong protic acid, as disclosed herein, provided an efficient aromatic acylation reaction. The invention thereby provides a process for preparing acylaromatics that avoids the use of aluminum chloride and other Lewis Acid reagents conventionally used for Friedel-Crafts aromatic acylation and that uses the carboxylic acid directly as the reactant rather than requiring its conversion to an acyl halide.

In one preferred embodiment, the present invention provides a process for the preparation of a para-acyl phenoxyethylamine of the formula

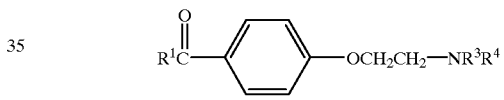

comprising reacting a 2-phenoxyethyl compound of the formula

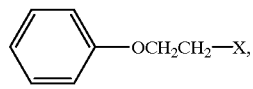

wherein X is a leaving group capable of substitution by an amine of the formula $HNR^3R^4$, with a carboxylic acid of the formula

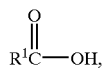

wherein $R^1$ is a hydrocarbyl group, in the presence of a reaction medium comprising polyphosphoric acid and a strong protic acid, to form a para-acyl phenoxyethyl intermediate of the formula

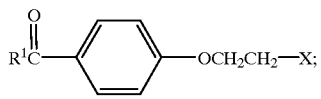

and reacting the para-acyl phenoxyethyl intermediate with an amine of the formula $HNR^3R^4$, wherein $R^3$ and $R^4$ are independently selected from hydrogen and hydrocarbyl groups, or $R^3$ and $R^4$ taken together form a divalent hydrocarbyl group, to form the para-acyl phenoxyethylamine. Thus, the invention provides a process for the preparation of 1-[4-[2-N,N-dimethyl-amino) ethoxy]phenyl]-2-phenyl-1-butanone, which is a para-acyl phenoxyethylamine compound of the above formula wherein $R^1$ is 1-phenylpropyl ($R^1CO_2H$ is 2-phenylbutyric acid) and $R^3$ and $R^4$ are each methyl ($HNR^3R^4$ is dimethylamine).

Employing the inventive aromatic acylation reaction the present invention provides a new, advantageous process for the preparation para-acyl phenoxyethylamines from inexpensive 2-phenoxyethanol, which is illustrated below for 1-[4-[2-(N,N-dimethylamino)ethoxy]phenyl]-2-phenyl-1-butanone:

Mesylation Reaction:

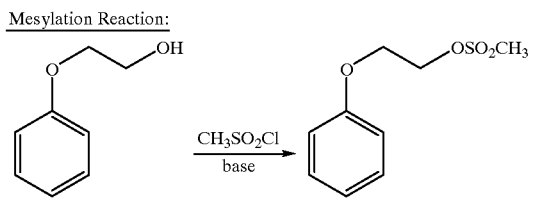

Acylation Reaction:

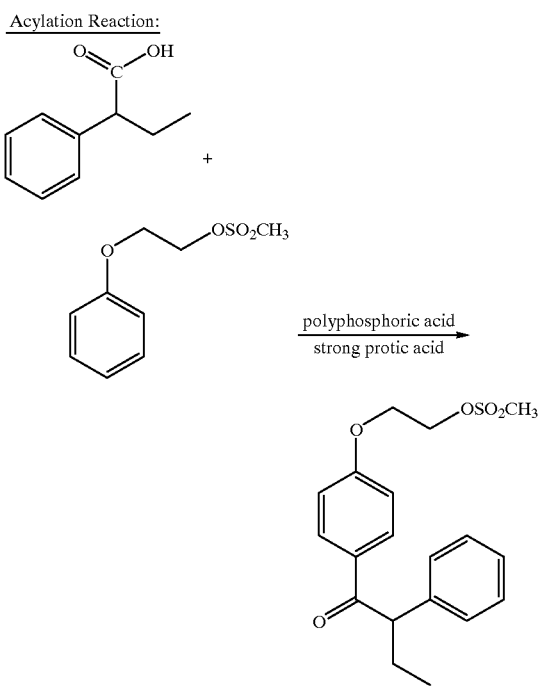

Substitution Reaction:

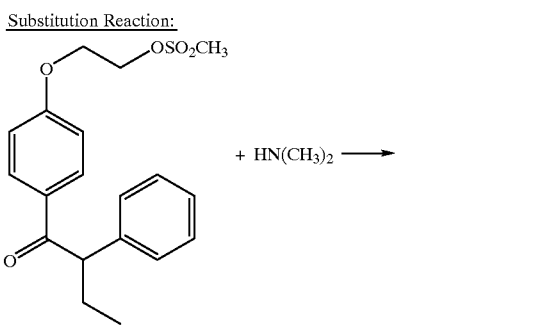

-continued

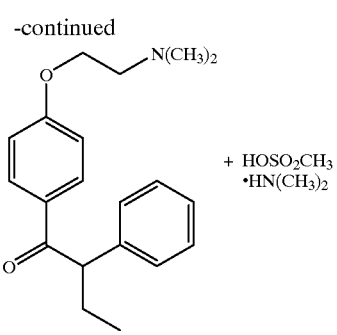

This new synthetic method for 1-[4-[2-(N,N-dimethylamino)ethoxy]-phenyl]-2-phenyl-1-butanone offers substantial advantages over known methods, including: (1) It uses inexpensive, easily handled raw materials; (2) There is no need for the toxic reagent 2-dimethylaminoethyl chloride used in the conventional process; (3) It uses of the free acid, 2-phenylbutyric acid, instead of the corresponding acid chloride; (4) It avoids the use of the Lewis acid reagent $AlCl_3$ and the associate waste products; (5) It is all liquid processing, since no solids are used or isolated except the final product; and (6) The three steps are easily adapted to a "one-pot" process and the resulting efficient use of reactors.

DETAILED DESCRIPTION OF THE INVENTION

The present invention provides a process for preparing acylaromatics of the formula $R^1C(=O)Ar^1$ from aromatic compounds of the formula $HAr^1$, wherein $Ar^1$ is an aryl group, and carboxylic acids of the formula $R^1C(=O)OH$, wherein $R^1$ is a hydrocarbyl group. Suitable aryl groups $Ar^1$ include carbocyclic aryl groups, having only carbon atoms in the aromatic ring system and heterocyclic aryl groups, having one or more heteroatoms in the aromatic ring system. Typical carbocyclic aryl groups have 6–14 carbon atoms in the aromatic ring system. Preferred carbocyclic groups are phenyl and substituted phenyl groups. Typical heterocyclic aryl groups have 5–13 atoms in the aromatic ring system which comprises carbon atoms and one or more heteroatoms. Preferred heteroatoms are oxygen, sulfur, and nitrogen, with the provision that when the heteroatom is nitrogen, it is preferred to be as the N-oxide derivative to provide reactivity towards the acylation reaction. Preferred heterocyclic aryl groups have 5 or 6 atoms in an aromatic ring comprising one or more heteroatoms selected from the group oxygen, sulfur, and nitrogen, benz-fused derivatives thereof, and substituted derivatives thereof. Examples of preferred heterocyclic aryl groups include pyridyl (as N-oxide), furyl, thiophenyl, pyrrolyl (as N-oxide), quinolinyl (as N-oxide), isoquinolinyl (as N-oxide), benzfuryl, benzthiophenyl, indolyl (as N-oxide), isoindolyl (as N-oxide), and substituted derivatives thereof.

Suitable substituents in substituted aryl groups $Ar^1$ are unreactive towards the reaction medium comprising polyphosphoric acid and a strong protic acid and and include alkyl (preferably $C_1$–$C_{12}$), alkenyl (preferably $C_2$–$C_{12}$), alkynyl (preferably $C_3$–$C_{12}$), alkoxy (preferably $C_1$–$C_{12}$), substituted alkoxy (preferably $C_1$–$C_{12}$), aryloxy, aryl, heteroaryl, F, Cl, Br, I, $SO_2$, SOR, and Si-trialkyl (preferably $C_1$–$C_{12}$), OH, $NO_2$, NHCO-alkyl (preferably $C_1$–$C_8$), CONH-alkyl (preferably $C_1$–$C_4$), CON-dialkyl (preferably $C_1$–$C_4$), CO-alkyl (preferably $C_1$–$C_{12}$), CO-aryl, CHCH $CO_2$-alkyl (preferably $C_1$–$C_{12}$), $CHCHCO_2H$, PO-diaryl, PO-dialkyl (preferably $C_1$–$C_8$), and trihalomethyl.

Preferred substituents in substituted aryl groups $Ar^1$ are pi-electron-donating donating substituents that are unreactive towards the reaction medium. These are well known to those skilled in the art and include, for example, hydrocarbyloxy groups, such as alkoxy, substituted alkoxy, aryloxy, substituted aryloxy, aryl, and substituted aryl. When the aryl group is substituted by a pi-electron donating substituent, acylation characteristically occurs at a hydrogen, designated H in $HAr^1$ that is para to the substituent. Particularly preferred are alkoxy substituents, whereby the acylaromatic product is apara-acyl alkoxyaromatic compound. Among alkoxyaromatic reactants are phenyl ethers of the formula left below, which react to give para-acylphenyl ether compounds of the formula right below,

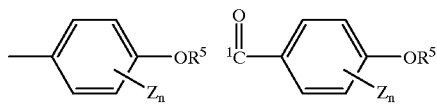

wherein $R^5$ is a hydrocarbyl group (preferably $C_1-C_{12}$), Z is a substituent selected from halo, hydrocarbyl, alkoxy, and aryloxy substituents, and n is an integer from 0 to 4, wherein when n is greater than 1, the Z substituents may be the same or different. In a most preferred embodiment, $R^5$ is alkyl (preferably $C_1-C_{12}$) and n=0.

Suitable carboxylic acids of the formula $R^1C(=O)OH$, wherein $R^1$ is a hydrocarbyl group include carboxylic acids wherein the hydrocarbyl group $R^1$ is substituted or unsubstituted. Preferably $R^1$ is a hydrocarbyl group having from 1 to 20 carbon atoms and from 1 to 10 heteroatoms other than hydrogen. In one embodiment, $R^1$ is a linear or branched alkyl group having from 1 to 12 carbon atoms, more preferably from 1 to 6 carbon atoms (e.g., methyl, ethyl, propyl, isopropyl), or a cycloalkyl group having from 3 to 12 carbon atoms, more preferably from 3 to 8 carbon atoms (e.g., cyclopropyl, cyclohexyl). In another embodiment, $R^1$ is an aryl group having from 5 to 14 carbon atoms, more preferably from 6 to 12 carbon atoms (e.g., phenyl). In one embodiment, $R^1$ is an aralkyl group having from 7 to 13 carbon atoms (e.g., benzyl). In one embodiment, $R^1$ is an alkaryl group having from 7 to 13 carbon atoms (e.g., tolyl).

In one embodiment, $R^1$ is a 2-arylhydrocarbyl group. Suitable 2-aryl-hydrocarbyl groups include those having the formula:

wherein $Ar^2$ is an aryl group and $R^2$ is hydrogen or a hydrocarbyl group. Suitable aryl groups $Ar^2$ include those suitable for $Ar^1$, described above. Suitable hydrocarbyl groups $R^2$ include those suitable for $R^1$, described above.

In one embodiment, $R^1$ is attached to, or is part of, the aromatic compound. In this way, an intermolecular reaction is possible, involving an aromatic hydrogen (the H in the formula $HAr^1$) and a carboxylic acid group (the COOH in the formula $R^1$—COOH). Such reactions are often useful for ring closure, as discussed above. Particularly preferred intramolecular embodiments are for the preparation of indanones and tetralones. This is illustrated for the unsubstituted parent compounds, indanone and tetralone, by the following equation (x=2 and x=3, respectively).

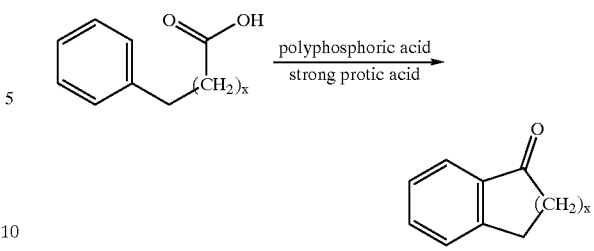

The acylation reaction of the present invention is conducted in a reaction medium comprising polyphosphoric acid and a strong protic acid. The term "reaction medium" is used herein in the conventional sense, and refers to the liquid medium in which the aromatic compound and the carboxylic acid react to produce the acylaromatic compound. The reaction medium need not bring about complete solution of the reactants or the product.

The term "polyphosphoric acid" is used herein in the conventional sense and refers to mixed oligomeric anhydrides of phosphoric acid of the general formula $HOP(O)_2(OP(O)_2)_m$—$OP(O)_2OH$, where m is an integer. Polyphosphoric acid is often characterized by its equivalent $H_3PO_4$ content, a number >100% by weight (115% $H_3PO_4$ is a common commercial composition) or by its equivalent $P_2O_5$ content, a number <100% by weight. These numbers are directly related to each other and to the average m in the oligomeric mixture. Polyphosphoric acids are common industrial products of phosphorus refining. They can also be produced by reacting $H_3PO_4$ with $P_2O_5$. Typical polyphosphoric acid compositions are viscous liquids at room temperature, conveniently fluid at 60° C., and stiff glasses at lower temperatures. Polyphosphoric acid is also referred to as "phospholeum".

The term "strong protic acid" is used in the conventional sense, except that polyphosphoric acid and phosphoric acid are specifically excluded for the purpose of this invention. A protic acid different from that provided by polyphosphoric acid must be provided. Suitable strong protic acids can be identified by routine experimentation following the procedures illustrated in the working Examples, below. Strong protic acids which may electrophilically react with the aromatic compound should be avoided. These are known to those skilled in the art and include, for example, sulfuric acid and nitric acid. Preferred strong protic acids are organic strong protic acids, for example hydrocarbylsulfonic acids and strong carboxylic acids. Suitable strong protic acids for use in the present invention have a $pK_a$ in aqueous solution of less than about 3. Preferred strong protic acids have a $pK_a$ in less than 2, and the most preferred strong protic acids have a $pK_a$ of 1.3 or less. Examples of suitable strong protic acids include, but are not limited to, methanesulfonic acid ($CH_3SO_3H$, $PK_a$ 1.3), trifluoromethanesulfonic acid ($CF_3SO_3H$, $PK_a$ -11), and trifluoroacetic acid ($CH_3CO_2H$, pKa 0.5). In a preferred embodiment, the strong protic acid is methanesulfonic acid.

The acylation reaction medium may include an additional solvent that is reaction-inert. By reaction-inert solvent is meant a solvent system which does not react with the reactants or products of the reaction, or react unfavorably with the reaction medium, which can be determined by routine experimentation. The term solvent system is used to indicate that a single solvent or a mixture of two or more solvents can be used. Representative solvents are aliphatic hydrocarbons such as pentane, hexane, heptane, dialkyl ethers; cyclic ethers, sulfolane, chlorinated hydrocarbons such as methylene chloride, dichloroethylene, carbon tetrachloride, and chloroform. Aromatic hydrocarbons that are less reactive that the aromatic compound to be acylated may be used by adjusting the reaction temperature and time such that no significant reaction of the aromatic hydrocarbon solvent occurs within the time that the aromatic reactant is converted. For example, the preferred phenyl ether reactants may be reacted in the presence of aromatic hydrocarbon solvents such as benzene, toluene, and xylene. The solvent system used need not bring about complete solution of the reactants.

In a preferred embodiment, the reaction medium consists essentially of polyphosphoric acid and the strong protic acid. In one embodiment, the reaction medium comprises polyphosphoric acid and a strong protic acid in a weight to weight ratio of from about 1:20 to about 20:1. In one embodiment, the reaction medium comprises polyphosphoric acid and a strong protic acid in a weight to weight ratio of from about 1:10 to about 10:1. In one embodiment, the reaction medium comprises polyphosphoric acid and a strong protic acid in a weight to weight ratio of from about 1:5 to about 5:1. In one embodiment, the reaction medium comprises polyphosphoric acid and a strong protic acid in a weight to weight ratio of from about 1:3 to about 3:1. In one embodiment, the reaction medium comprises polyphosphoric acid and a strong protic acid in a weight to weight ratio of from about 1:2 to about 2:1. For example, a reaction medium prepared from 32.44 g polyphosphoric acid (115% $H_3PO_4$) and 64.88 g of methanesulfonic acid has a polyphosphoric acid to strong protic acid weight to weight ratio of 1:2.

Suitable ratios of reactants to the polyphosphoric acid and to the strong protic acid in the reaction medium can be determined by routine experimentation. At a minimum, the amount of polyphosphoric acid should provide P—O—P anhydride equivalents (calculable from the %H3PO4) equal to the moles of the carboxylic acid. Typically, on this basis, the polyphosphoric acid is used in excess of the carboxylic acid. Typically, the strong protic acid is also used in molar excess relative to the carboxylic acid. In the preferred embodiment wherein the reaction medium consists essentially of polyphosphoric acid and the strong protic acid, an excess of the strong protic acid provides a stirrable reaction medium. In this embodiment, the strong protic acid is preferably provided in a mole ratio of at least 3:relative to the carboxylic acid. It is also preferably provided in a more ratio of less than 9:1 relative to the carboxylic acid for the volumetric efficiency of the reaction.

Either reactant, the aromatic compound or the carboxylic acid, may be the limiting reactant and this choice can respond to other considerations, such as which is the more costly reactant to provide and which is more readily separated or removed to an acceptable level from the product. Generally the mole ratio of the aromatic compound to the carboxylic acid is in the range 0.5:1 to 2:1. Typically, the aromatic compound and the carboxylic acid are initially present in the range of 1:1.2 to 1.2–1 mole ratio. In a preferred embodiment, the carboxylic acid is present in 10% excess on a molar basis.

The reaction temperature should be sufficient for the reaction to proceed at a practical rate. Suitable and optimal reaction temperatures depend on a number of other parameters, including the concentrations and reactivities of the specific reactants, polyphosphoric acid composition, the nature and strength of the strong protic acid, and can be readily determined by routine experimentation. In typical embodiments, the reaction is conducted at a temperature in the range from about 50° C. to 120° C., preferably from about 60° C. to 100° C.

The order of addition of the reaction components is not critical. All the reaction components can be added prior to any heating to the reaction temperature, or one or more components may be added when the other components have be brought to the desired reaction temperature. The preferred order of addition for any specific embodiment can be determined by routine experimentation with a view towards both reaction performance and chemical engineering considerations.

The acylaromatic compound can be recovered and isolated by known methods. For typical acylaromatic products, the reaction mixture is hydrolyzed to separate the spent polyphosphoric acid and the strong protic acid in an aqueous solution from the product in an organic solution.

For the preparation of para-acylphenoxyethylamines by the invention, the aromatic compound reactant is a 2-phenoxyethyl compound of the formula

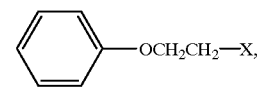

wherein X is a leaving group that is compatible with the acylation reaction conditions and capable of substitution by the amine that will provide the desired para-acyl phenoxyethylamine compound, which may be determined by routine experimentation. Typical X are the halides susceptible to nucleophilic aliphatic substitution, chloride, bromide, and iodide, and hydrocarbyl-sulfonates, such as methanesulfonate, benzene sulfonate, p-toluenesulfonate, and p-nitrophenylsulfonate. In an especially preferred embodiment, X is methanesulfonate X=$CH_3SO_3$—), which is also known as mesyloxy or mesylate.

These reactants can be prepared from phenol, by alkylation with a 2-X-ethyl alkylating agent, or from 2-phenoxyethanol by a reagent that converts the OH group to the leaving group X, in either case by conventional methods known in the art. For example, 2-phenoxyethyl chloride (X=Cl) has been prepared from phenol and 1,2-dichloroethane and from 2-phenoxyethanol and thionyl chloride (McCague, 1986). Example 1 below describes the preparation of 2-phenoxyethyl methanesulfonate from 2-phenoxyethanol and methane-sulfonyl chloride.

Acylation of such a 2-phenoxyethyl compound, bearing the leaving group X, by the process of the present invention provides a para-acyl phenoxyethyl intermediate of the formula

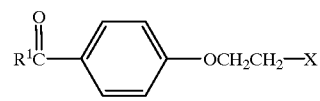

wherein $R^1$ and X are as described above. This intermediate (an acylaromatic product of the present invention) is separated from the polyphosphoric acid and strong protic acid of the reaction medium by conventional means, and may be further purified or isolated, or carried forward without further purification or isolation.

The para-acyl phenoxyethyl intermediate is then reacted with an amine of the formula $HNR^3R^4$, wherein $R^3$ and $R^4$ are independently selected from hydrogen and hydrocarbyl groups, or $R^3$ and $R^4$ taken together form a divalent hydrocarbyl group, to form the para-acyl phenoxyethylamine of the following formula.

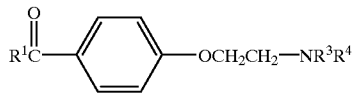

Suitable amines include ammonia ($R^3=R^4=H$), primary amines ($R^3=H$, $R^4$=hydrocarbyl), and secondary amines ($R^3$=hydrocarbyl and $R^4$=hydro-carbyl and they may be the same or different). Suitable hydrocarbyl groups for $R^3$ and $R^4$ include those described above for $R^1$. Additionally, for secondary amines $R^3$ and $R^4$ taken together may form a divalent hydrocarbyl radical, whereby the secondary amine is a cyclic amine. In one embodiment, $R^3$ and $R^4$ taken together form a divalent organic group having from 2 to 20 carbon atoms, preferably from 2 to 10 carbon atoms, more preferably from 2 to 6 carbon atoms (e.g., ethylene, propylene, butylene, pentylene). Examples of suitable cyclic amines include pyrrolidines, pyrroles, oxazolines, imidazoles, N-monosubstituted imidazoles, piperidines, piperazines, N-monosubstituted piperazines, morpholines, and the like, and their C-substituted derivatives.

Preferred amines are secondary amines. Particularly preferred are dialkylamines and saturated cyclic amines. An especially preferred dialkylamine is dimethylamine. An especially preferred saturated cyclic amine m pyrroidine.

Either reactant, the para-acyl phenoxyethyl intermediate or the amine may be the limiting reactant and this choice can respond to other considerations, such as which is the more costly reactant to provide and which is more readily separated or removed to an acceptable level from the product. Generally, the amine is less expensive and more easily separated from the product and is used in excess to drive the reaction of the more valuable para-acyl phenoxyethyl intermediate to completion. In evaluating how much amine is required, it should be remembered that a second equivalent of amine is neutralized by the HX coproduct of the reaction. A further excess of amine is often desirable to minimize the formation of a quaternary ammonium salt by competitive reaction of the para-acyl phenoxyethyl intermediate with the para-acyl phenoxyethylamine product instead of with the amine. Typically the mole ratio of the amine to the para-acyl phenoxyethyl intermediate is in the range 1:1 to 20:1, and preferably in the range 2:1 to 10:1.

The reaction of the para-acyl phenoxyethyl intermediate with the amine may be conducted without a solvent, with an excess of the amine as solvent, with an additional solvent that is reaction-inert, or with a mixture of excess amine base and a solvent that is reaction inert. By reaction-inert solvent is meant a solvent system which does not react with the reactants or products of the reaction. The term solvent system is used to indicate that a single solvent or a mixture of two or more solvents can be used. Representative solvents are aromatic hydrocarbons such as benzene, toluene, xylene; aliphatic hydrocarbons such as pentane, hexane, heptane; acetonitrile; dialkyl ethers; cyclic ethers, polar aprotic solvents such as dimethylformamide, dimethyl-acetamide, N-methylpyrollidone, and sulfolane, chlorinated hydrocarbons such as methylene chloride, dichloroethylene, carbon tetrachloride, and chloroform, and mixtures thereof. The solvent system used need not bring about complete solution of the reactants. Preferred solvents include the amine and mixtures of the amine and a hydrocarbon solvent. Water may also be present in the solvent system. Amines that are commonly available as aqueous solutions, like ammonia and dimethylamine, may be used directly as such solutions.

The reaction temperature is not critical, but is preferably sufficient for the reaction to proceed at a practical rate. Suitable and optimal reaction temperatures depend on a number of other parameters, including the concentrations and reactivities of the specific amine and the specific the para-acyl phenoxyethyl intermediate and the nature of the solvent, and can be readily determined by routine experimentation. In typical embodiments, the reaction is conducted at a temperature in the range from about 20° C. to 200° C., and preferably from about 50° C. to 120° C. When the amine has a significant vapor pressure over the reaction mixture at the reaction temperature, the reaction may be run under pressure containment to maintain the amine in the reaction mixture.

The order of addition of the reaction components is not critical. All the reaction components can be added prior to any heating, or one or more components may be added when the other components have be brought to the desired reaction temperature. The preferred order of addition for any specific embodiment can be determined by routine experimentation with a view towards both reaction performance and chemical engineering considerations.

The para-acyl phenoxyethylamine can be recovered and isolated by known methods.

EXAMPLES OF THE INVENTION

Without further elaboration, it is believed that one skilled in the art can, using the preceding description, utilize the present invention to its fullest extent. The following specific examples are intended merely to illustrate the invention and not to limit the scope of the disclosure or the scope of the claims in any way whatsoever.

Example 1

Preparation of 1-[4-[2-(N,N-dimethylamino)ethoxy] phenyl]-2-phenyl-1-butanone via acylation of 2-phenoxyethyl methanesulfonate with 2-phenyl-butyric acid.

Mesylation of 2-phenoxyethanol

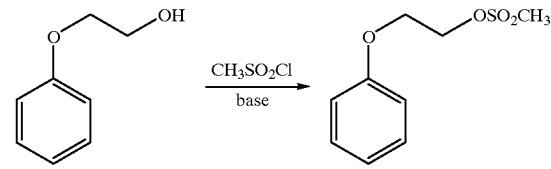

To a 500 mL three neck flask equipped with a thermometer, 25 mL addition funnel, mechanical stirrer, and positive nitrogen bubbler was added 27.63 g (200 mmol) 2-phenoxyethanol, 250 mL toluene and 37 mL (250 mmol) triethylamine. The flask was placed in an ice bath and 17 mL (220 mmol) methanesulfonyl chloride was added dropwise from the addition funnel over 30 minutes while maintaining the temperature of the reaction mixture below 25° C. After completion of the addition, the mixture was stirred for 3 hours at room temperature. 125 mL water were added to dissolve the precipitated triethylamine hydrochloride and to hydrolyze the excess methanesulfonyl chloride. The biphasic system was stirred for 30 minutes and the lower aqueous phase was removed. The organic phase was then stirred with 125 mL 5% hydrochloric acid for 30 minutes, and the lower aqueous phase was removed. The flask was fitted with a distillation head and toluene was distilled out of the mixture under aspirator vacuum. The temperature in the stillpot was increased from room temperature to a maximum of 44° C. over the course of the the distillation. The remaining orange oil, comprising 2-phenoxyethyl methanesulfonate and 5% toluene (1H NMR) was used directly in the subsequent acylation reaction.

Acylation of 2-phenoxyethyl methanesulfonate with 2-phenylbutyric acid

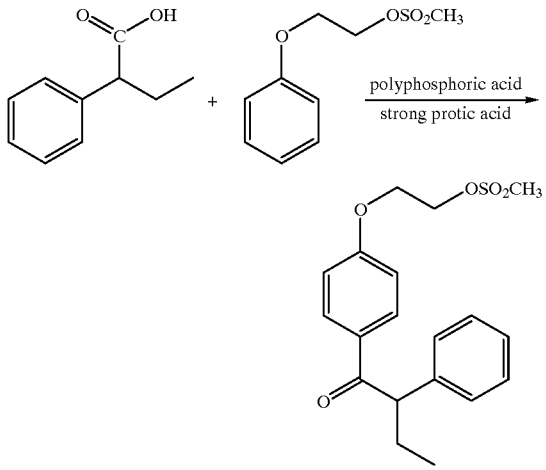

To the 2-phenoxyethyl methanesulfonate oil in the three-neck flask was added 32.44 g polyphosphoric acid (115% $H_3PO_4$), 64.88 g (675 mmol) methanesulfonic acid and 36.86 g (220 mmol) 2-phenylbutyric acid. The flask was fitted with a reflux condenser, the system was purged with nitrogen and the mixture was heated to 75° C. under positive nitrogen pressure. The mixture became a homogeneous liquid at 50° C. The solution was stirred at 75° C. for 2 hours. It was then cooled to 30° C. and 125 mL toluene was added. The mixture was then placed in an ice bath and 125 mL water was added dropwise allowing the temperature to rise to 55° C. The biphasic system was stirred for 3 hours at 50° C. The lower aqueous phase was removed and 125 mL 10% aqueous sodium hydroxide (NaOH) was added to the organic phase. This mixture was stirred for 30 minutes and the aqueous phase was removed. The remaining organic phase, comprising 1-[4-[2-(methanesulfonxy) ethoxy-]phenyl]-2-phenyl-1-butanone, was used in the subsequent amine substitution step.

Reaction of 1-4-[2-(methanesulfonxy) ethoxylphenyl]-2-phenyl1-1-butanone with dimethylamine

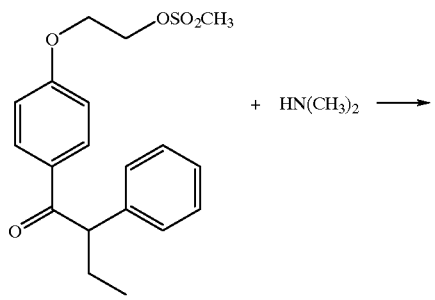

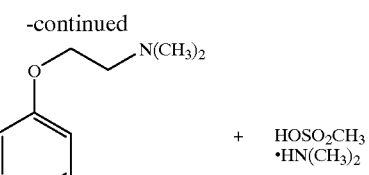

The organic phase comprising 1-[4-[2-(methanesulfonxy) ethoxy]phenyl]-2-phenyl-1-butanone was transferred into a glass Fischer Porter pressure bottle. A magnetic stirring bar was placed in the bottle and 100 mL (800 mmol) 40% aqueous dimethylamine solution was added, and the bottle was closed with a pressure head with gauge. The biphasic mixture was vigorously stirred and heated to 60° C. The internal pressure rose to 10 psig (~170 kPa). The mixture was stirred at this temperature for 5 hours. Initially, the aqueous phase is lighter than the organic phase; during the reaction the two layers invert. The bottle were cooled in an ice bath until no overpressure remained, opened and emptied into a separatory funnel. The aqueous layer was removed and the organic layer was poured into a 500 mL Erlenmeyer flask. 120 mL 10% aqueous hydrochloric acid was added and the mixture stirred for 30 minutes at 50° C. 32 mL methanol was added and the mixture was transferred into a separatory funnel. The aqueous phase was removed and the organic layer transferred into a 500 mL three neck flask equipped with mechanical stirrer and thermometer. Aqueous and organic phases separated over about 15 minutes. 120 mL n-heptane was added and the flask placed in an ice bath. Under stirring, 28.6 g 50% aqueous sodium hydroxide (NaOH) was added dropwise (to a stablized pH 12) and the mixture stirred at 40° C. for 30 minutes. The aqueous phase was removed and the flask was equipped with a Dean Stark trap. The mixture was heated and the remaining water was removed from the heptane by azeotropic distillation. Distillation started at 85° C., the water was removed within 45 minutes and the stillpot reached a final temperature of 106° C. When no more water could be collected, the solution was cooled first to room temperature and then placed in a ethylene glycol cooling bath. The temperature was lowered to −20° C., a few seed crystals of 1-[4-[2-(N,N-dimethylamino)ethoxy]phenyl]-2-phenyl-1-butanone were added, and the mixture was stirred at −20° C. for 30 minutes. The crystallized product was vacuum filtered dried under vacuum at room temperature for 12 hours, to constant weight, to yield 52.0 g (167 mmol) of 1-[4-[2-(N,N-dimethylamino)ethoxy]phenyl]-2-phenyl-1-butanone (311.43 g/mol) as a colorless solid. (m.p. 49–50° C. $^1$H-NMR (300.13 MHz, $CDCl_3$/TMS): d=0.89 (t, 3H); 1.77–1.91 (m, 11); 2.09–2.26 (m, 1H1); 2.32 (s, 6); 2.71 (t, 2H); 4.08 (t, 2H); 4.39 (t, 1H); 6.85–6.90 (m, 211); 7.16–7.32 (m, 5H1); 7.92–7.99 (m, 2H). The purity measured by HPLC vs. reference standard was 99.2%. The yield based on 2-phenoxyethanol was 83%.

This example illustrates the process of the invention wherein an acylaromatic, in this case a para-acylphenyl ether and specifically a para-acyl phenoxyethyl intermediate as defined above, is prepared by reacting an aromatic compound, in this case a phenyl ether and specifically a 2-phenoxyethyl compound of the formula Ph—$CH_2CH_2$ —X as defined above, with a carboxylic acid, in this case a 2-aralkanoic acid, in the presence of a reaction medium comprising polyphosphoric acid and a strong protic acid, in this case methanesulfonic acid. It further illustrates the process of the invention wherein apara-acyl phenoxyethylamine, is prepared from the 2-phenoxyethyl compound of the formula Ph—$CH_2CH_2$—X via the acylation reaction and the further step of reacting the para-acyl phenoxyethyl intermediate with an amine. It further illustrates inventors' highly efficient process for the preparation of para-acyl phenoxyethylamine, in this case 1-[4-[2-(N,N-dimethylamino)ethoxy]phenyl]-2-phenyl-1-butanone, from 2-phenoxyethanol.

Example 2

Preparation of 1-[4-[2-(methanesulfonxy)ethoxy]phenyl]-2-phenyl-1-ethanone by acylation of 2-phenoxyethyl methanesulfonate with 2-phenylacetic acid

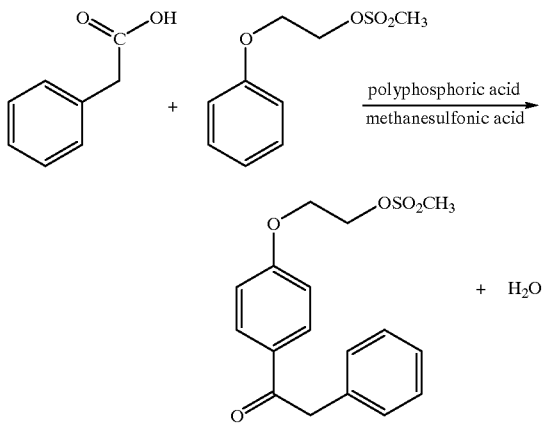

The oil comprising 2-Phenoxyethyl methanesulfonate was prepared as described above in Example 1. The acylation and workup procedure was identical to that of Example 1 with the exception that 30.26 g (220 mmol) 2-phenylacetic acid was reacted instead of the 2-phenylbutyric acid. The organic layer obtained by the workup procedure was cooled to 25° C. and stirred at this temperature for 1 hour. The resulting crystallized product was filtered, washed with toluene and dried under vacuum at 40° C. to yield 53.18 g (159 mmol) of the 4-(2-mesyloxyethoxy)phenyl benzylketone as a tan colored solid. Yield: 80% on 2-phenoxyethanol.

This Example illustrates the inventive process for the preparation of an acylaromatic as does Example 1 but with another carboxylic acid reactant.

Example 3

Preparation of 1-(2.3-dihydrobenzofuran-5-yl)-2-phenylbutanone by acylation of 2.3-dihydrobenzofuran with 2-phenylbutyric Acid

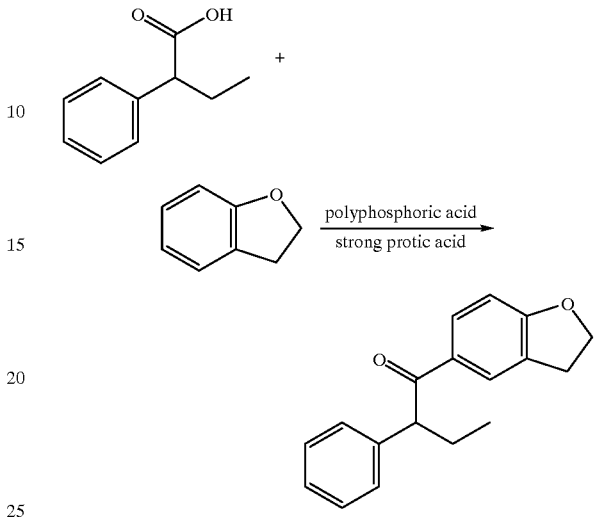

1.20 g (10 mmol) 2,3-dihydrobenzofuran was stirred with 3.24 g methanesulfonic acid, 1.62 g polyphosphoric acid, and 1.84 g (11 mmol) 2-phenylbutyric acid. The mixture was heated to 75° C. for 2 hours, cooled to room temperature, then 5 mL toluene and 5 mL water were added dropwise. The biphasic system was stirred for 3 hours at 50° C., the aqueous phase was removed, and the organic phase was washed with 10 mL 10% aqueous sodium hydroxide. The aqueous phase was removed, the toluene phase was dried over magnesium sulfate, and the solvent was evaporated from it to yield 1.83 g (6.87 mmol) of 1-(2,3-dihydrobenzofuran-5-yl)-2-phenylbutanone as a yellow liquid (1H-NMR). Yield: 69% based on 2,3-dihydrobenzofuran.

This example illustrates the process of the invention wherein an acylaromatic, in this case apara-acylphenyl ether is prepared by reacting an aromatic compound, in this case a cyclic henyl ether, with a carboxylic acid in the presence of a reaction medium comprising polyphosphoric acid and a strong protic acid, in this case methanesulfonic acid, which has a pKa of 1.3.

Example 4

Preparation of 1-(2.3-dihydrobenzofuran-5-yl)-2-phenylbutanone by acylation of 2.3-dihydrobenzofuran with 2-phenylbutyric Acid The procedure was identical to that of Example 3 with the exceptions that 2.6 mL of trifluoroacetic acid was used instead of the methanesulfonic acid and the reaction time at 75° C. was 20 hours. HPLC analysis confirmed the same product formed as formed by the procedure of Example 3.

This example illustrates the process of the invention as does Example 3, but with another strong protic acid, in this case trifluoroacetic acid, which has a pKa value of 0.5.

Example 5

Preparation of 1-(2 .3-dihydrobenzofuran-5-yl)-2-phenylbutanone by acylation of 2.3-dihydrobenzofuran with 2-phenylbutyric Acid The procedure was identical to that of Example 4 with the exception that 3.0 mL of trifluoromethanesulfonic acid was used instead of the trifluoroacetic acid. HPLC analysis confirmed the same product formed as formed by the procedure of Example 3.

This example illustrates the process of the invention as does Example 3, but with another strong protic acid, in this case trifluoromethanesulfonic acid, which has a pKa value of −11.

Example 6

Preparation of 1[L4-(2-chloroethoxy)phenyl]-2-phenyl-1-butanone by acylation of 2-phenoxyethyl chloride with 2-phenylbutyric acid

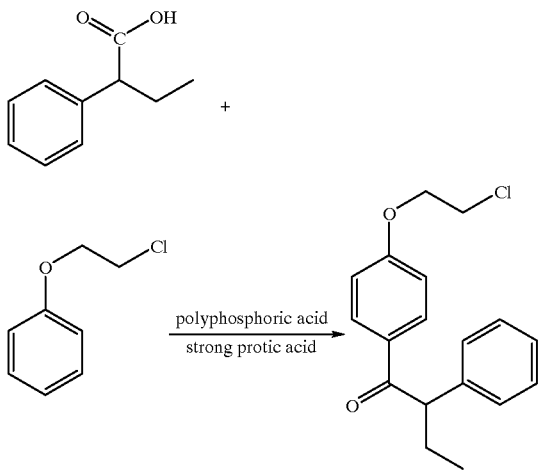

500 mg 2-phenoxyethyl chloride was mixed with 2.0 g methanesulfonic add, 600 mg polyphosphoric acid, and 600 mg 2-phenylbutyric acid. The mixture was heated to 75° C. for 1 hour, with stirring. 5 mL toluene was added, followed by 5 mL water, then the biphasic mixture was stirred for 3 hours at 50° C. The aqueous phase was removed and the organic phase was extracted with 5 mL 5% sodium hydroxide solution. $^1$H-NMR analysis of the toluene layer confirmed the product to be 1-[4-(2-chloro-ethoxy)-phenyl]-2-phenyl-1-butanone.

This Example illustrates the acylation process of the invention as does Example 1, but with another X group, chloride. In view of the report of McCague, 1986 describing the reaction of the product of this Example with dimethylamine to produce 1-[4-[2-(N,N-dimethylamino)ethoxy] phenyl]-2-phenyl-1-butanone, this Example also constructively illustrates the process of the invention wherein apara-acyl phenoxyethylamine, is prepared from the 2-phenoxyethyl compound of the formula Ph—CH$_2$CH$_2$—X, in this case X=Cl, via the acylation reaction and the further step of reacting the para-acyl phenoxy-ethyl intermediate with an amine.

Example 7

Preparation of 1-[4-[2-N,N-dimethylamino)ethoxy] phenyl]-2-phenyl-1-butanone via acylation of 2-phenoxyethyl bromide with 2-phenylbutyric acid Acylation of 2-phenoxyethyl bromide with 2-phenylbutyric acid

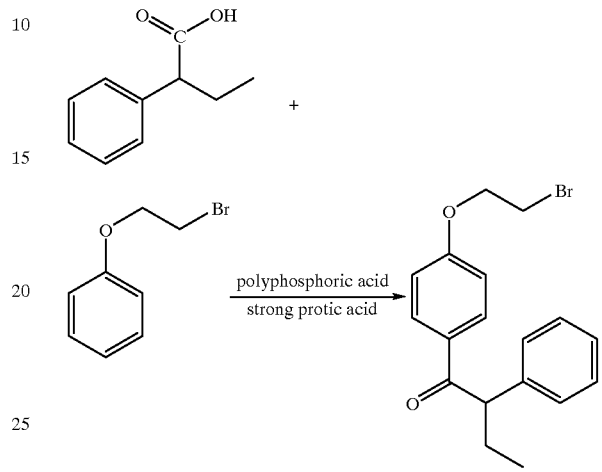

929 mg 2-phenoxyethyl bromide, 1.0 mL methanesulfonic acid, 750 mg polyphosphoric acid, and 834 mg 2-phenylbutyric acid were reacted and worked up as described in Example 6. $^1$H-NMR analysis of the resulting toluene solution confirmed the product to be 1-[4-(2-bromo-ethoxy)-phenyl]-2-phenyl-1-butanone.

Reaction of 1-L4-(2-bromoethoxy)phenyl-2-phenyl-1-butanone with dimethylamine

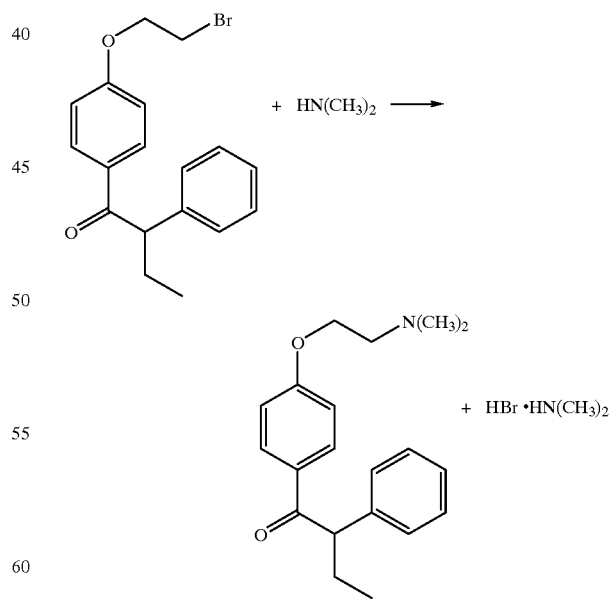

The touene solution of 1-[4-(2-bromo-ethoxy)-phenyl]-2-phenyl-1-butanone was reacted with excess 40% aqueous dimethylamine with vigorous stirred in a closed pressure vessel at 40° C. for 10 hours. Analysis of the resulting toluene solution thin-layer chromatography and $^1$H-NMR showed complete formation of 1-[4-[2-(N,N-dimethylamino)ethoxy]phenyl]-2-phenyl-1-butanone.

This Example illustrates the invention as does Example 1, but with another X group, bromide.

Example 8

Acylation of naphthalene with 2-phenylbutyric acid 592 mg (4.62 mmol) naphthalene was mixed with 1.5 g methanesulfonic acid, 750 mg polyphosphoric acid, and 834 mg (5.08 mmol) 2-phenylbutyric acid. The mixture was heated to 75° C. for 2 hours with stirring. 5 mL toluene was added followed by 5 mL water, then the biphasic mixture was stirred for 3 hours at 50° C. The aqueous phase was removed and the organic phase was extracted with 5 mL 10% aqueous sodium hydroxide solution, dried over magnesium sulfate, and evaporated in vacuo to remove the solvent and yield 700 mg yellow oil. GC/MS analysis showed the presence of two isomeric monoacylated napthalene products in 30 and 22 area%, and 5 area% of a diacylated napthalene product.

This Example illustrates the process of the invention for a polynuclear aromatic reactant, naphthalene. Compared to previous examples, it also illustrates the process of the invention for an aromatic compound that does not bear an alkoxy or similar pi-electron donating substituent.

Example 9

Preparation of indanone by the intramolecular aromatic acylation of 3-phenylpropionic acid 695 mg (4.62 mmol) 3-phenylpropionic acid was mixed with 1.5 g methanesulfonic acid and 750 mg polyphosphoric acid. The mixture was heated to 75° C. for 2 hours with stirring. 5 mL toluene was added followed by 5 mL water, then the biphasic system was stirred for 3 hours at 50° C. The aqueous phase was removed and the organic phase was extracted with 5 mL 10% aqueous sodium hydroxide solution, dried over magnesium sulfate, and evaporated in vacuo to remove the solvent and yield 200 mg yellow oil. GC/MS analysis showed the presence of 2-indanone in 21 area %.

This Example illustrates the acylation process of the invention for the intramolecular acylation of aralkanoic acids. It further illustrates the invention for an aromatic substrate that does not bear pi-electron donating substituents comparable to alkoxy substituents.

The present invention has been shown by both description and examples. The Examples are only examples and cannot be construed to limit the scope of the invention. One of ordinary skill in the art will envision equivalents to the inventive process described by the following claims which are within the scope and spirit of the claimed invention.

References

McCague, "The use of perfluorotolyl protecting group in the synthesis of pure Z and E isomers of 4-hydroxytamoxifen {1-[4-(2-eimethylaminoethoxy)phenyl-1-(4-hydroxyphenyl)-2-phenyl-1-butene}," J. Chem. Res., Miiiprint, 0771 (1986).

Yamato et al., "Organic reactions catalyzed by solid superacids 5. Perfluorinated sulfonic acid resin (Nafion-H) catalyzed intramolecular Friedel-Crafts acylation," J. Org. Chem., Vol. 56, pp.3955–2957 (1991).

Chiche et al., "Acylation over cation-exchanged montmorillonite," J. Molecular Catalysis, Vol. 42, pp. 229–235 (1987).

Eaton et al., "Phosphorus pentoxide-methanesulfonic acid. A convenient alternative to polyphosphoric acid," J. Org. Chem., Vol. 38, No. 23, pp. 4071–4073 (1973).

Galli, "Acylation of arenes and heteroarenes with in situ generated acyl trifluoroacetates," Synthesis: Communications, pp. 303–304 (1979).

Smyth et al., "Industrially viable alternative to the Friedel-Crafts acylation reaction: tamoxifen case study," Org. Process Research & Develop., Vol. 1, pp.264–267 (1997).

Tiovola et al., "Tri-phenyl alkene derivatives and their preparation and use," U.S. Pat. No. 5,491,173, issued Feb. 13, 1996.

We claim:

1. A process for the preparation of an acylaromatic compound of the formula $R^1C(=O)Ar^1$ comprising reacting an aromatic compound of the formula $HAr^1$, wherein $Ar^1$ is an aryl group, with a carboxylic acid of the formula $R^1C(=O)OH$, wherein $R^1$ is a hydrocarbyl group, in the presence of a reaction medium comprising polyphosphoric acid and a strong protic acid, to form the acylaromatic compound.

2. The process of claim 1 wherein the strong protic acid is selected from strong protic acids having a $pK_a$ value less than 3.

3. The process of claim 1 wherein the strong protic acid is selected from methanesulfonic acid, trifluoromethanesulfonic acid, and trifluoroacetic acid.

4. The process of claim 1 wherein the strong protic acid is methanesulfonic acid.

5. The process of claim 1 wherein the reaction medium consists essentially of the polyphosphoric acid and the strong protic acid.

6. The process of claim 5 wherein the polyphosphoric acid and the strong protic acid are present in the reaction medium at a weight:weight ratio of between 20:1 and 1:20.

7. The process of claim 1 wherein the aryl group, $Ar^1$, is a phenyl group comprising a pi-electron donating substituent para to the hydrogen atom denoted H in the formula $Ar^1H$.

8. The process of claim 7 wherein the pi-electron donating substituent is an alkoxy substituent.

9. The process of claim 8 wherein the aromatic compound is an alkoxyphenyl compound, the strong protic acid is methanesulfonic acid, and the acylaromatic compound is a para-acyl alkoxyaromatic compound.

10. A process for the preparation of a para-acylphenyl ether compound of the formula

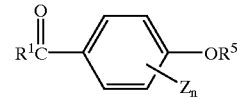

comprising reacting a phenyl ether compound of the formula

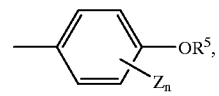

wherein
  $R^5$ is a hydrocarbyl group,
  Z is a substituent selected from halo, hydrocarbyl, alkoxy, and aryloxy substituents, and n is an integer from 0 to 4, wherein when n is greater than 1, the Z substituents may be the same or different, with a carboxylic acid of the formula

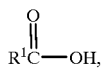

wherein $R^1$ is a hydrocarbyl group, in the presence of a reaction medium comprising polyphosphoric acid and a strong protic acid, to form the para-acylphenyl ether compound.

11. The process of claim 10 wherein the strong protic acid is selected from strong protic acids having a pKa value less than 3.

12. The process of claim 10 wherein the strong protic acid is selected from methanesulfonic acid, trifluoromethanesulfonic acid, and trifluoroacetic acid.

13. The process of claim 10 wherein the strong protic acid is methanesulfonic acid.

14. The process of claim 10 wherein the reaction medium consists essentially of the polyphosphoric acid and the strong protic acid.

15. The process of claim 14 wherein the polyphosphoric acid and the strong protic acid are present in the reaction medium at a weight:weight ratio of between 20:1 and 1:20.

16. The process of claim 10 wherein n is 0.

17. The process of claim 10 wherein $R^5$ is a 2-substituted ethyl group.

18. The process of claim 17 wherein $R^5$ is 2-methanesulfonxy.

19. The process of claim 10 wherein $R^1$ is a 2-arylhydrocarbyl group.

20. A process for the preparation of apara-acyl phenoxyethylamine of the formula

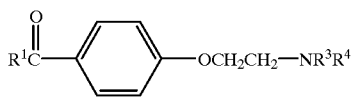

comprising:
reacting a 2-phenoxyethyl compound of the formula

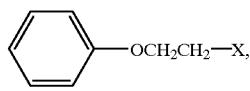

wherein X is a leaving group capable of substitution by an amine of the formula $HNR^3R^4$, with a carboxylic acid of the formula

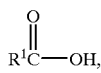

wherein $R^1$ is a hydrocarbyl group, in the presence of a reaction medium comprising polyphosphoric acid and a strong protic acid, to form a para-acyl phenoxyethyl intermediate of the formula

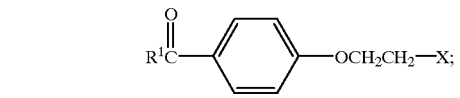

and
reacting the para-acyl phenoxyethyl intermediate with an amine of the formula $HNR^3R^4$ wherein
$R^3$ and $R^4$ are independently selected from hydrogen and hydrocarbyl groups, or
$R^3$ and $R^4$ taken together form a divalent hydrocarbyl group, to form the para-acyl phenoxyethylamine.

21. The process of claim 20 wherein the leaving group X is a halide or a hydrocarbylsulfonate group.

22. The process of claim 21 wherein the hydrocarbylsulfonate group is methanesulfonate.

23. The process of claim 20 wherein the 2-phenoxyethyl compound is provided by reacting 2-phenoxyethanol with a reagent that converts the OH group of the 2-phenoxyethanol to the leaving group X.

24. The process of claim 23 wherein the reagent is methanesulfonyl chloride and the leaving group X is methanesulfonate.

25. The process of claim 20 wherein the strong protic acid is selected from strong protic acids having a pKa value less than 3.

26. The process of claim 20 wherein the strong protic acid is selected from methanesulfonic acid, trifluoromethanesulfonic acid, and trifluoroacetic acid.

27. The process of claim 20 wherein the strong protic add is methanesulfonic acid.

28. The process of claim 20 wherein the reaction medium consists essentially of the polyphosphoric acid and methanesulfonic acid.

29. The process of claim 28 wherein the polyphosphoric acid and the strong protic acid are present in the reaction medium at a weight:weight ratio of between 1:10 and 10:1.

30. The process of claim 20 wherein $R^1$ is a 2-arylhydrocarbyl group.

31. The process of claim 30 wherein the 2-arylhydrocarbyl group is selected from 2-aralkyl groups of the formula

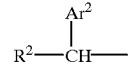

wherein $Ar^2$ is an aryl group and $R^2$ is selected from hydrogen and hydrocarbyl groups.

32. The process of claim 20 wherein the amine is a secondary amine.

33. The process of claim 32 wherein the secondary amine is selected from dialkyl amines and saturated cyclic amines.

* * * * *